(12) United States Patent
Hirsh

(10) Patent No.: US 8,479,739 B2
(45) Date of Patent: Jul. 9, 2013

(54) SYSTEM AND METHOD FOR MANAGING DIFFICULT AIRWAYS

(75) Inventor: Robert Hirsh, Merion Station, PA (US)

(73) Assignee: The Cooper Health System, Camden, NJ (US)

( * ) Notice: Subject to any disclaimer, the term of this patent is extended or adjusted under 35 U.S.C. 154(b) by 2279 days.

(21) Appl. No.: 11/292,767

(22) Filed: Dec. 2, 2005

(65) Prior Publication Data

US 2007/0129603 A1   Jun. 7, 2007

(51) Int. Cl.
*A61M 16/00* (2006.01)
*A42B 1/04* (2006.01)
*A42B 1/24* (2006.01)
*A61B 1/00* (2006.01)
*A61B 1/267* (2006.01)

(52) U.S. Cl.
USPC ............ 128/207.14; 128/200.26; 128/207.15; 2/171; 2/209.13; 600/120; 600/131; 600/184; 600/185; 600/186; 600/187; 600/188; 600/189; 600/190; 600/191; 600/192; 600/193; 600/194; 600/195; 600/196; 600/197; 600/198; 600/199; 600/200

(58) Field of Classification Search
USPC .......... 128/200.26, 207.14, 207.15; 600/120, 600/131, 184–200; 2/171, 209.13
See application file for complete search history.

(56) References Cited

U.S. PATENT DOCUMENTS

| | | | |
|---|---|---|---|
| 4,249,539 A | 2/1981 | Vilkomerson et al. | |
| 4,431,006 A | 2/1984 | Trimmer et al. | |
| 5,003,300 A | 3/1991 | Wells | |
| 5,095,888 A | 3/1992 | Hawley | |
| 5,484,416 A | 1/1996 | Gittings | |
| 5,645,519 A * | 7/1997 | Lee et al. | 600/114 |
| 5,733,241 A | 3/1998 | King | |
| 5,767,820 A | 6/1998 | Bassett et al. | |
| 5,775,322 A * | 7/1998 | Silverstein et al. | 128/207.14 |
| 5,949,388 A | 9/1999 | Atsumi et al. | |
| 5,951,461 A | 9/1999 | Nyo et al. | |
| 5,973,728 A * | 10/1999 | Levitan | 348/77 |
| 6,053,871 A | 4/2000 | Cockburn | |
| 6,146,402 A | 11/2000 | Munoz | |
| 6,539,942 B2 | 4/2003 | Schwartz et al. | |
| 6,652,453 B2 | 11/2003 | Smith et al. | |
| 6,685,634 B1 * | 2/2004 | Fry | 600/300 |
| 6,832,986 B2 | 12/2004 | Chhibber et al. | |
| 6,929,600 B2 * | 8/2005 | Hill | 600/120 |
| 7,052,456 B2 * | 5/2006 | Simon | 600/120 |

FOREIGN PATENT DOCUMENTS

WO    WO 98/15310    4/1998
WO    WO 03/103482   12/2003

* cited by examiner

FOREIGN PATENT DOCUMENTS

*Primary Examiner* — Patricia Bianco
*Assistant Examiner* — Nihir Patel
(74) *Attorney, Agent, or Firm* — Michael B. Fein; Eckert Seamans Cherin & Mellott, LLC

(57) ABSTRACT

A system and method for endotracheal intubation of airways are disclosed. A malleable stylet having a distal end and a proximal end, a charged coupled device (CCD) at the distal end and a transmitter, at or near the proximal end or connected to the proximal end of the stylet with connectors, transmits video to a visualization device comprising a receiver means, a display means, and a display support adapted to be worn on an operator in a position so that the operator can view the display with one eye while simultaneously viewing the airway directly. The display support is typically worn on the head of a physician. A second display can be worn by a student or observer. In some instances, the transmitter means and receiver means are wireless.

16 Claims, 3 Drawing Sheets

SYSTEM AND METHOD FOR MANAGING DIFFICULT AIRWAYS

FIELD OF THE INVENTION

This invention relates generally to the field of endotracheal intubation of patients by a medical professional, and, in some aspects, relates to intubation of difficult airways.

BACKGROUND OF THE INVENTION

A conventional method of endotracheal intubation is to first use a MacIntosh or Miller laryngoscope to move the patient's tongue out of the way, visualize the vocal cords, and then to insert an endotracheal tube (ETT) with a malleable stylet inside. Once the ETT is placed in proper position, the stylet is removed and the ETT is connected, for example, by means of a 15 mm connector, to a circle system to supply oxygen and remove carbon dioxide.

For the situation of "difficult airways," i.e., when the uvula can not be seen by inspection with the mouth wide open and the tongue extended, various alternative procedures have been used. The "difficult airways" situation arises frequently when the patient has a short mandible, impaired neck mobility, a short neck, trismus of the jaw, or a swollen tongue. Other situations of difficult airways arise when the patient is obese or is wearing a halo cervical fixation device because of a cervical fracture. Such alternative approaches include the Bullard laryngoscope, the reverse Seldinger technique, or the blind, Fast Track insertion device.

A conventional method of endotracheal intubation of difficult airways is to use a fiberoptic scope. Fiberoptic scopes allow the operator to visualize structures at the distal end of the scope by looking through a lens at the proximal end of the fiberoptic scope. However, some fiberoptic scopes are difficult to precisely control, making it difficult to visualize the vocal cords. Also, some fiberoptic scopes require the use of a special skill set which is not ordinarily used on a daily basis. Furthermore, fiberoptic scopes typically do not create by themselves a pocket of air inside the pharynx through which structures can be visualized. In some cases, operators of fiberoptic scopes see pink rather than the airway. When the tip of the fiberoptic lens is up against the tissues of the pharyngeal walls, against the tongue, or in the vallecula, the operator will see pink rather than the airway. Furthermore, in some situations when the operator focuses one eye through the eyepiece and closes the other eye, the operator may lose the natural, global, intuitive perspective ordinarily gained from looking directly into the mouth with a conventional rigid laryngoscope blade of known extension.

A need exists, therefore, for intubation systems and methods for using same. A further need exists for an intubation system which allows the medical professional to easily and continuously view the laryngeal area during the procedure without having to look away from the ETT being inserted.

SUMMARY OF THE INVENTION

It is an object of the present invention to provide an improved system and method for endotracheal intubation of airways.

It is another object of the invention to provide a system which avoids the problems associated with fiberoptic scopes currently used for visualization of trachea during endotracheal intubations. In some aspects, the present invention allows simultaneous access to two useful perspectives when performing endotracheal intubation of difficult airways.

These and other objects as will become apparent from the following disclosure and drawings are achieved by the present invention which comprises, in some aspects, a system for endotracheal intubation of airways comprising (A) a malleable stylet having a distal end and a proximal end, a imaging means, for example, a charged coupled device (CCD), at the distal end and a wireless transmitter at, near, or connected to the proximal end, and (B) a visualization device comprising a wireless receiver means, a display means, and a display support adapted to be worn on an operator in a position so that the operator can view the display with one eye while simultaneously viewing the airway directly. In some aspects the imaging means can be a sensor for recording images other than a CCD.

In some aspects, the invention comprises a method of endotracheal intubation of a patient airway comprising inserting the malleable stylet into the lumen of an ETT and using it to view the anatomy forward of the distal end of the ETT on the display means. The CCD on the distal end of the stylet acts as a camera which broadcasts the view from the patient's larynx to the display means being worn by the person doing the intubation. The broadcast can be received by other persons wearing display devices, for example, doctors, nurses, medical residents, students, and the like. A special stylet with video means on the distal end is used and the image seen by the video means is seen on a display worn by an operator. The term "worn" is meant to include wearing a headset, a headband, or any other means for supporting a display device on a person, for example, clipping a display device to eyeglasses.

The stylet can be a tube with a lumen through the center, or it can be a solid wire. In some instances, the stylet may have more than one lumen, for example, in embodiments which include an optional illumination means, a separate lumen may be provided to carry the conductor means such as wires from the source of electrical power to the illumination means such as an LED or xenon lamp. The stylet is primarily constructed of a malleable material, including without limitation, copper or aluminum. In some embodiments, the stylet is coated with plastic material, for example, polyethylene molded in the dimensions of the stylet. In some embodiments, a CCD imaging means at the distal end is connected to a wireless transmitter at the proximal end by means of one or more cables within the stylet lumen or on the between the stylet and the plastic covering, when present. In some embodiments, the coaxial cable terminates at a connector at the proximal end of the stylet, and the wireless transmitter is in a housing assembly which has a connector designed to mate with the connector at the proximal end of the stylet. The CCD and wireless transmitter in the stylet assembly may be powered by a battery. In some embodiments, the battery is within the wireless transmitter assembly. The visualization device may also include a power supply. In some embodiments, the power supply is a rechargeable battery. If the stylet has a lumen, it can be used to introduce a thin, flexible guide wire through the vocal cords and into the trachea under direct vision. This can facilitate tube placement under difficult circumstances.

The wireless transmitter may be permanently connected to the stylet or within the stylet itself. In some embodiments, the transmitter is located in a separate housing along with a power supply and antenna. In some embodiments, the transmitter is part of the stylet itself rather than in a separate housing connected to the stylet by plug and socket connectors. The housing may have a socket or plug at one end which matches and engages a corresponding plug or socket on the stylet. The transmitter housing may include a switch so that the transmitter can be turned on and off, and it may have means for easy replacement of the battery, or it may have a separate connector for recharging the battery. In some embodiments, the wireless transmitter housing does not come in contact with the patient and so does not have to be sterilized. The housing may be sterilizable, if desired.

The stylet can be designed and engineered for single use and therefore need not be sterilizable after the use, or the stylet can be designed to be sterilized and reused.

At the distal end of the stylet, the imaging means, for example a CCD or other type of video chip, is in some embodiments covered with plastic, for example a plastic lens, and may also include a source of illumination such as a xenon flash lamp or an LED. In some embodiments, the source of illumination provides a white light. In some embodiments, the LED can have one level of illumination for direct visualization below the vocal cords and a different level of illumination to trans-illuminate the trachea, which can be easily seen on the patient's neck in a dark room, thereby assisting the operator to confirm appropriate ETT placement. The source of illumination can use the same battery as the CCD or can employ a separate battery. In some embodiments, the level of illumination provided for illumination of the trachea is at least two, three, four, or five times greater than the illumination provided for illumination below the vocal cords. The source of illumination can optionally be automatically keyed at a predetermined rate, or modulated in a pre-determined way, to help the operator see the trans-illumination of the trachea by inspection from the outside of the neck even in a sub-optimally darkened room, such as an ICU bed. By keying the high intensity light source used for trans-illumination, the operator can avoid thermal injury to the inner lining of the trachea. An optical diffuser, to make the light project radially outward from the long axis of the stylet in 360 degrees, can be molded into the clear plastic covering of the stylet. In some embodiments, the stylet battery is rechargeable. The source of illumination at the tip of the stylet can, in some embodiments, thereby serve two purposes, to illuminate the trachea so it can be imaged with the imaging means, for example a CCD camera lens/assembly, and to trans-illuminate the trachea so that the neck near the Adam's apple is seen to glow red in a darkened room, thereby confirming proper tube placement, especially in those circumstances where the mouth and trachea are filled with blood, as in trauma. In this circumstance the xenon flash lamp may be selected for trans-illumination since it flashes and creates a powerful light of brief duration which can be seen through the neck even in a room not optimally darkened. In some embodiments, the system includes a controller or other subsystem to control the lamp flash. In some embodiments, the flash is modulated in a pre-determined fashion so that the illumination from within the trachea is easier to see from outside the neck, especially in a sub-optimally darkened room.

In some embodiments, the material used to construct the stylet is malleable. In some embodiments, the stylet is rigid and is made of aluminum or copper. In some embodiments, the stylet is covered with plastic sheathing. The plastic sheathing can be any of the types known in the art for use in medical applications, including, for example, polyethylene. In some embodiments, cables connecting the CCD at the distal end to a plug or socket at the proximal end can be run through a lumen of the malleable stylet when the stylet is a tube, which can have one or more lumens, or can be run on the outside of the stylet when it is a solid wire, and then covered by the sheathing. In some embodiments, the cable is a micro coaxial cable.

In some embodiments, the display support is designed to place a display in front of one eye of the operator. In some embodiments, the display is designed to place the display to the side of the operator's line of sight so that the operator may view the patient directly with both eyes while at the same time viewing the display showing the view from the distal end of the stylet peripherally. In these embodiments, the operator need only shift his gaze peripherally without moving his head to appreciate both perspectives. This is similar to the use of a rear-view mirror when driving a car. In some embodiments, cables to power the optional LED can be run through the same lumen as between the stylet and the covering.

The display support may include one or more LCDs or other suitable display devices. In some embodiments, the display support has one LCD display fixedly positioned in the support so that it is not in the direct line of sight of the operator or physician. In some embodiments, the LCD or LCDs may be supported so that they can be flipped down, rotated, or otherwise adjusted so that they can be positioned in the direct line of sight at the operator's option.

In some embodiments, the stylet and display system are wirelessly connected. In some embodiments, the stylet and display system are wired together.

In some embodiments, the system of the invention may be used with conventional laryngoscopes, for example Macintosh or Miller blades. In some embodiments, the system may also be used with conventional endotracheal tubes.

BRIEF DESCRIPTION OF THE DRAWINGS

An embodiment of the invention is illustrated in the drawings and will be described in more detail below with reference thereto. The illustrated embodiment is only one example of the invention and the description thereof is not intended to imply a limitation on the invention. The invention is capable of considerable modification, alteration and equivalents in form and function.

DESCRIPTION OF THE INVENTION

Figure 1:
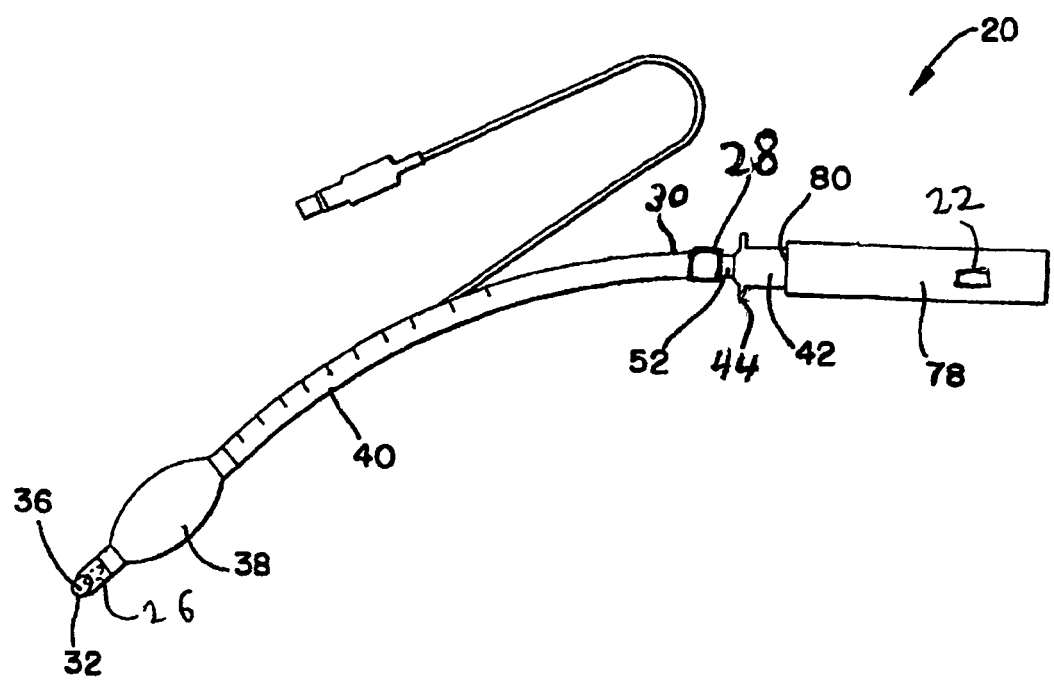
FIG. 1 shows a side view of an embodiment of an endotracheal tube partially enclosing a malleable stylet including a CCD at the distal end and a wireless transmitter housing at the proximal end.

Referring first to FIG. 1 of the drawings, an embodiment of an ETT-stylet-wireless transmitter assembly 20 is shown. The assembly 20 includes an ETT 40, stylet 52, and wireless transmitter housing 78. The wireless transmitter housing 78 includes a plug 80 which engages socket assembly 42, which in turn is press fit to the stylet 52. The wireless transmitter housing 78 locks onto the socket assembly 42 and can be unlocked by pressing a tab (not shown) on the socket assembly 42.

The stylet is made of aluminum tube in this embodiment. In some embodiments, the stylet is made of other malleable materials such as copper. The stylet can be solid wire instead of tubular.

The stylet is of a size and shape so it can be inserted through the center of the ETT 40, as illustrated, so that the stylet distal end 36 is close to the ETT distal end 32. The stylet should fit smoothly and easily into the ETT 40, and then the ETT 40 with stylet 52 inside can be bent into a curve or other shape, as desired by the operator doing the intubation procedure. The term "operator" is meant to include medical professionals or any other person trained to perform an intubation. The stylet must remain slidable in the ETT 40 center channel so that it can easily be removed by gentle pulling in the proximal direction after the ETT 40 has been placed. ETTs are manufactured in various sizes, depending on whether for pediatric, adult, or other uses. In some embodiments, the stylet 52 element of the invention is slightly longer than the longest commercial ETT 40.

The ETT 40 has a proximal end 30, a distal end 32, and a first mounting element 28 on the proximal end 30. The first mounting element 28 is commonly known as a "port" or "fitting." The ETT 40, made of plastic or other appropriate material, also defines a lumen 36 between the ends. The distal end 32 of the ETT 40 is inserted into the trachea of a patient. An inflatable cuff 38 is provided near the distal end 32 of the ETT 40. The cuff 38 is inflated after the ETT distal end 32 is in place within the trachea. Once inflated, the cuff 38 provides a seal between the tracheal wall and the ETT 40. The ETT 40 is open at both ends to allow oxygen or anesthetic gas to flow through the lumen 36 and into the patient's lungs once the ETT 40 is inserted into the trachea and connected to an oxygen or gas supply.

The location of the ETT distal end 32 with respect to the patient's bronchi is important for proper intubation. The present invention helps to locate the ETT tube 40 accurately within the patient's trachea by providing an image of the endotracheal area to the operator during the intubation procedure.

In some embodiments, the ETT 40 is supplied with the first mounting element 28 on the proximal end 30. The first mounting element 28 may be attached to the ETT 40 in any manner that provides a seal between the ETT 40 and the first mounting element 28.

Figure 2:
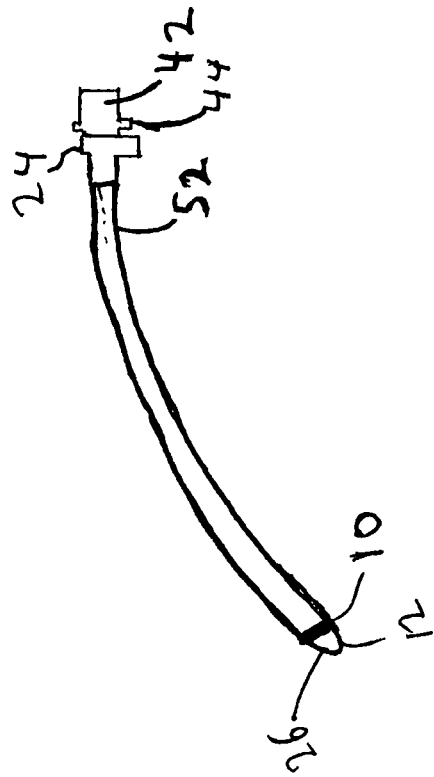
FIG. 2 shows a side view of an embodiment of a malleable stylet having a CCD at the distal end according to the invention.

Referring now to FIG. 2, a stylet 52 is shown having a CCD 10 at the distal end 26. The stylet 52 is a hollow aluminum tube covered over its entire length with polyethylene 12. The polyethylene 12 covers the CCD 10, and is clear so as not to impede the CCD 10. In some embodiments, less than the full length of the stylet is covered with a suitable material, for example polyethylene or polypropylene. In some embodiments, the CCD 10 can be covered by a lens (not illustrated).

Figure 3:
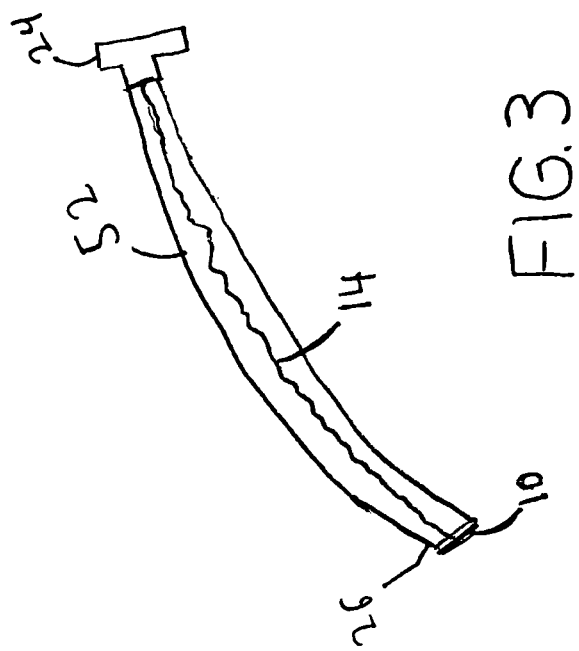
FIG. 3 shows a cross-sectional view of the embodiment of the stylet illustrated in FIG. 2.

FIG. 3 shows a cross-sectional view of a stylet 52 tube, with the CCD 10 at the distal end 26, connected by a cable 14 running through the lumen of the stylet tube to a stylet fitting 24 which, in turn, fits within socket assembly 42 (shown in FIG. 2). In FIG. 3, the covering is not illustrated. The covering is optional and other types of covering and other materials for the covering can be used. Many types of cable can be used including, without limitation, micro coaxial cables.

Figure 4:
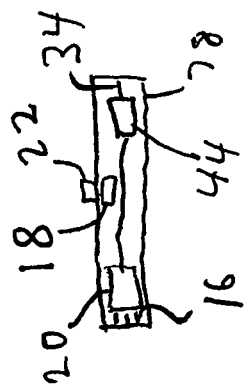
FIG. 4 shows a cross-sectional view of wireless transmitter housing.

FIG. 4 shows a cross-section of wireless transmitter housing 78 having a plug with prongs 16, battery 18, switch 22, and wireless transmitter assembly 44, connected to antenna 34. All of the necessary control apparatus and software are in transmitter assembly 44. The housing 78 fits on socket assembly 42 and snaps in when tab 44 engages. To disassemble, tab 44 is pressed and transmitter housing 78 is pulled in the proximal direction. The wireless transmitter broadcasts video from the CCD during the intubation procedure so that the operator can view the patient's tracheal area. In some embodiments not shown, an LED is included near the CCD to illuminate the tracheal area. LED's may be driven by power from battery 18 via wiring through the stylet lumen 36. The wireless transmitter housing 78 may be reusable since it does not come in contact with the patient, but the stylet can be either disposable or it can be sterilized and reused.

Figure 5:
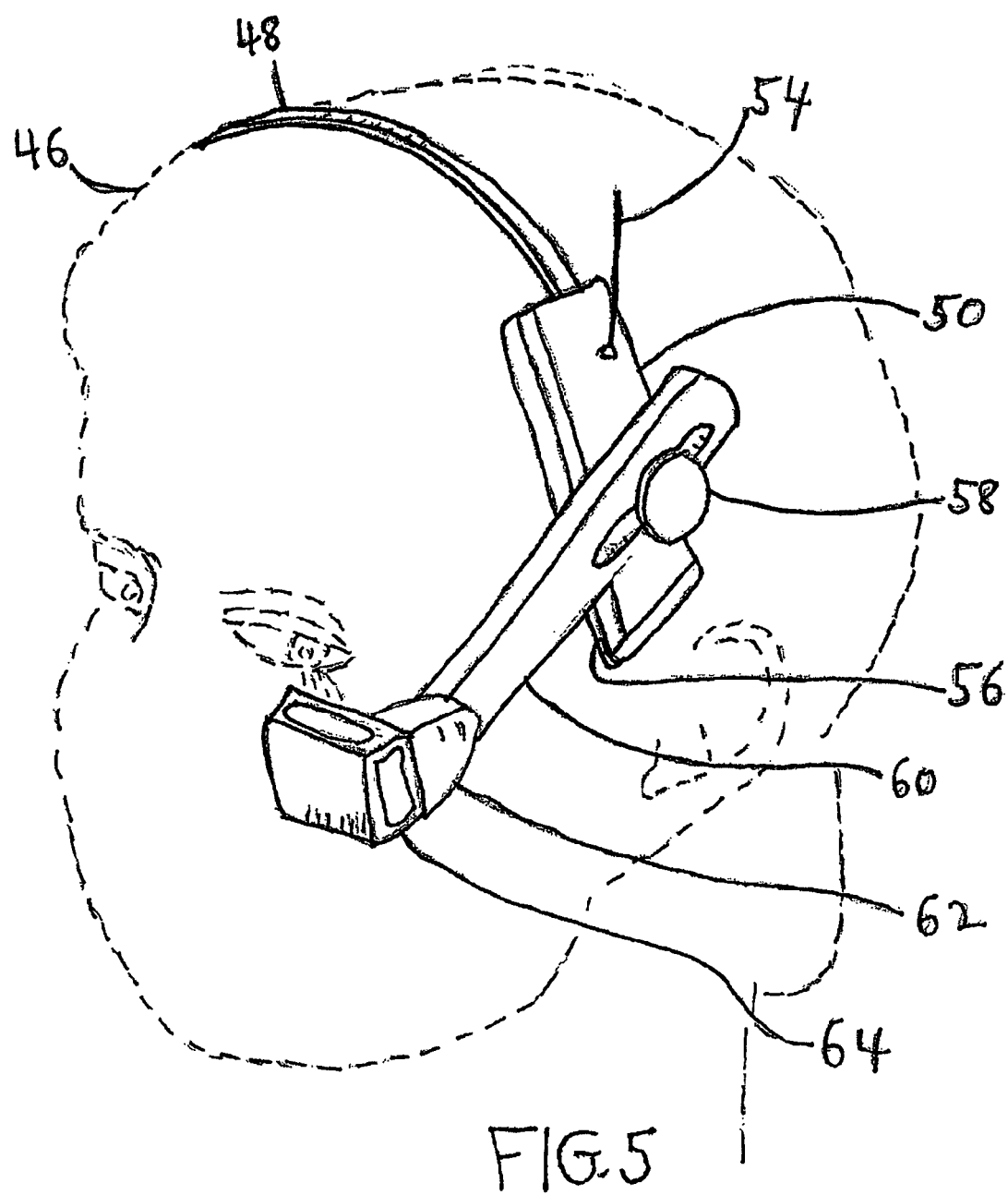
FIG. 5 shows a perspective view of a visualization device comprising a wireless receiver and an LED display supported on a headset, shown on a human operator.

FIG. 5 shows a perspective view of a wireless headset according to some embodiments of the invention on an operator 46, the headset having a headband member 48 which spans the top or back of the operator's head, a wireless receiver housing 50 which includes a battery, a controller and driver (not shown), and an antenna 54 for receiving the signal from the wireless transmitter 44 (FIG. 2). Foam 56 is provided on the housing 50 and also at the other end of the headband 48 (not shown). The illustrated foam is the type conventionally used in the headset art. A tightening screw 58 is provided to hold the display support rod 60 at a desired position. The display member 64 includes an LCD (on the side opposite the view) and is adjustable in relation to the support rod 60. The physician may adjust the LCD with regard to brightness, and may adjust the LCD display position to that which is most comfortable and convenient. The headset of this embodiment is designed to allow the physician 46 to view the patient with both eyes at all times, but also to see the LCD which shows the anatomy forward of the CCD 10 (FIG. 2.

While the invention has been described and illustrated in sufficient detail that those skilled in this art can readily make and use it, various alternatives, modifications, and improvements should become readily apparent without departing from the spirit and scope of the invention. All cited references are hereby incorporated by reference.

What is claimed is:

1. A system for endotracheal intubation of human airways comprising (A) a headset having a display means, adapted to be worn by an operator; (B) an endotracheal tube having lumen, a distal end adapted to enter an airway, and a proximal end, (B) a malleable stylet having a distal end and a proximal end, adapted to fit within the lumen of the endotracheal tube and to maintain the tube in a desired shape, the stylet having a charged coupled device (CCD) at the distal end capable of receiving visual images of a human airway distal to the distal end of the stylet, and (C) means to display the visual images of the human airway received by the CCD on the display means wherein the transmitter means is wireless and the receiver means is wireless, and the transmitter means and receiver means employ a Bluetooth wireless protocol.

2. A method of endotracheal intubation of a patient airway comprising (A) providing an endotracheal tube (ETT) having a lumen, (B) providing a malleable stylet having a distal end and a proximal end, having imaging means at the distal end, (C) inserting the stylet into the lumen of the ETT and shaping the ETT as desired; (D) providing a visualization device comprising a display means and a display support; (E) guiding the ETT into the proper position in the patient's trachea while simultaneously viewing the patient airway and an image of the patient airway distal to the imaging means on the display means, wherein an operator wears the visualization device, and an observer wears a second visualization device, each of the visualization devices adapted to receive a signal from the imaging means.

3. A system for endotracheal intubation of human airways comprising (A) a headset having a display means, adapted to be worn by an operator; (B) an endotracheal tube having lumen, a distal end adapted to enter an airway, and a proximal end, (B) a malleable stylet having a distal end and a proximal end, adapted to fit within the lumen of the endotracheal tube and to maintain the tube in a desired shape, the stylet having a charged coupled device (CCD) at the distal end capable of receiving visual images of a human airway distal to the distal end of the stylet, and (C) means to display the visual images of the human airway received by the CCD on the display means wherein the means (C) comprises a wireless transmitter in or on the stylet, a wireless receiver in or on the headset, means to connect the CCD to the wireless transmitter, and means to connect the wireless receiver to the display means.

4. The system of claim 3 wherein the stylet is adapted for single use.

5. The system of claim 3 wherein the stylet is sterilizable.

6. The system of claim 3 wherein the display support comprises an adjustable headband adapted to support the display means out of the direct line of sight of the operator.

7. The system of claim 3 wherein the display is an LCD screen.

8. The system of claim 3 wherein the stylet is constructed of a rigid, malleable material.

9. The system of claim 3 wherein the stylet is constructed of aluminum or copper.

10. The system of claim 3 wherein the means (C) to display the visual images received by the CCD on the display means comprises a wire connecting the stylet to the display means.

11. The system of claim 3 further comprising (D) illumination means at or near the distal end of the stylet to trans-illuminate the airway.

12. The system of claim 11 wherein the illumination means is (D) a xenon flash lamp or a white LED at or near the distal end of the stylet to trans-illuminate the airway.

13. The system of claim 3 further comprising (D) a xenon flash lamp or a white LED at or near the distal end of the stylet and (E) means to key or modulate the flash lamp or LED, thereby trans-illuminating the airway.

14. The system of claim 3 further comprising (D) a xenon flash lamp or a white LED at or near the distal end of the stylet and (E) means to key or modulate the flash lamp or LED, and (F) optical diffuser means to direct light emitted from the lamp or LED radially outward 360 degrees from the long axis of the stylet.

15. The system of claim 3 comprising a lumen in the stylet and a thin, flexible guide wire within the lumen in the stylet, wherein the guide wire can be moved past the vocal cords and into the trachea under direct vision, and moving the ETT over the stylet and guide wire into the trachea.

16. A system for endotracheal intubation of human airways comprising (A) a headset having a display means adapted to be worn by an operator; (B) an endotracheal tube having lumen, a distal end adapted to enter an airway, and a proximal end, (B) a malleable stylet having a distal end and a proximal end, adapted to fit within the lumen of the endotracheal tube and to maintain the tube in a desired shape, the stylet having a charged coupled device (CCD) capable of receiving visual images of an airway distal to the distal end of the stylet, and (C) means to display the visual images received by the CCD on the display means comprising a wireless transmitter in or on the stylet, a wireless receiver in or on the headset, means to connect the CCD to the wireless transmitter, means to connect the wireless receiver to the display means; wherein the system further comprises a xenon flash lamp or white LED at or near the distal end of the stylet and means to key or modulate the flash lamp or LED, and an optical diffuser means to direct light emitted from the lamp or LED radially outward 360 degrees from the long axis of the stylet.

* * * * *